(12) United States Patent
Ross et al.

(10) Patent No.: US 7,625,998 B2
(45) Date of Patent: Dec. 1, 2009

(54) CYTOKINE POLYPEPTIDES AND ANTIBODIES CONTAINING A SIGNAL SEQUENCE FOR THE ATTACHMENT OF GLYCOSYLPHOSPHATIDYLINOSITOL

(75) Inventors: Richard Ross, Sheffield (GB); Jon Sayers, Sheffield (GB); Peter Artymiuk, Sheffield (GB)

(73) Assignee: Asterion Limited, Sheffield (GB)

( * ) Notice: Subject to any disclaimer, the term of this patent is extended or adjusted under 35 U.S.C. 154(b) by 15 days.

(21) Appl. No.: 10/552,388

(22) PCT Filed: Apr. 7, 2004

(86) PCT No.: PCT/GB2004/001572

§ 371 (c)(1),
(2), (4) Date: Oct. 7, 2005

(87) PCT Pub. No.: WO2004/090135

PCT Pub. Date: Oct. 21, 2004

(65) Prior Publication Data

US 2006/0205926 A1    Sep. 14, 2006

(30) Foreign Application Priority Data

Apr. 9, 2003 (GB) .................. 0308088.4
Oct. 16, 2003 (GB) .................. 0324235.1

(51) Int. Cl.
  *C07K 14/475* (2006.01)
(52) U.S. Cl. ...................... 530/350; 530/402
(58) Field of Classification Search .............. None
  See application file for complete search history.

(56) References Cited

U.S. PATENT DOCUMENTS 6,136,563 A    10/2000    Olson et al.

FOREIGN PATENT DOCUMENTS

| WO | WO 96/34105 A1 | 10/1996 |
| WO | WO 01/96565 A2 | 12/2001 |
| WO | WO 02/083851 A2 | 10/2002 |
| WO | WO 03/017944 A2 | 3/2003 |

OTHER PUBLICATIONS

Benting et al. (1999), The Journal of Cell Biology, vol. 146, No. 2, pp. 313-320.*
Mikayama et al. Proc. Natl. Acad. Sci. USA vol. 90, pp. 10056-10060.*
Voet et al. Biochemistry John Wiley & Sons, Inc., pp. 126-128 and 228-234.*
Mikayama et al. Proc. Natl. Acad. Sci. USA vol. 90, pp. 10056-10060, (1993).*
Voet et al. Biochemistry John Wiley & Sons, Inc., pp. 126-128 and 228-234, (1990).*
Benting et al., "N-Glycans Mediate the Apical Sorting of a GPI-Anchored, Raft-Associated Protein in Madin-Darby Canine Kidney Cells," *J. Cell Biol.* 146:313-320 (1999).
Brostedt et al., "Characterization of Dimeric Forms of Human Pituitary Growth Hormone by Bioassay, Radioreceptor Assay, and Radioimmunoassay," *Acta Endocrinol.* 122:241-248 (1990).
Da Costa et al., "Production of the Thyrotrophin Receptor Extracellular Domain as a Glycosylphosphatidylinositol-Anchored Membrane Protein and Its Interaction with Thyrotrophin and Autoantibodies," *J. Biol. Chem.* 273:11874-11880 (1998).
Guadiz et al., "The Carboxyl Terminus of *Pneumocystis carinii* Glycoprotein A Encodes a Functional Glycosylphosphatidylinositol Signal Sequence," *J. Biol. Chem.* 273:26202-26209 (1998).
Meyers (ed.), "Molecular Biology and Biotechnology. A Comprehensive Desk Reference, Cytokines," pp. 200-204, 392-397, 474-476, and 789-793 (1995).

* cited by examiner

*Primary Examiner*—Prema Mertz
(74) *Attorney, Agent, or Firm*—Crowell & Moring LLP

(57) ABSTRACT

The invention relates to chimeric recombinant polypeptides, preferably therapeutic polypeptides, for example cytokines or antibodies, which are engineered to include a signal sequence for the attachment of glycosylphosphatidylinositol; cells expressing said polypeptides and methods to manufacture said polypeptides.

5 Claims, 7 Drawing Sheets

Figure 1:
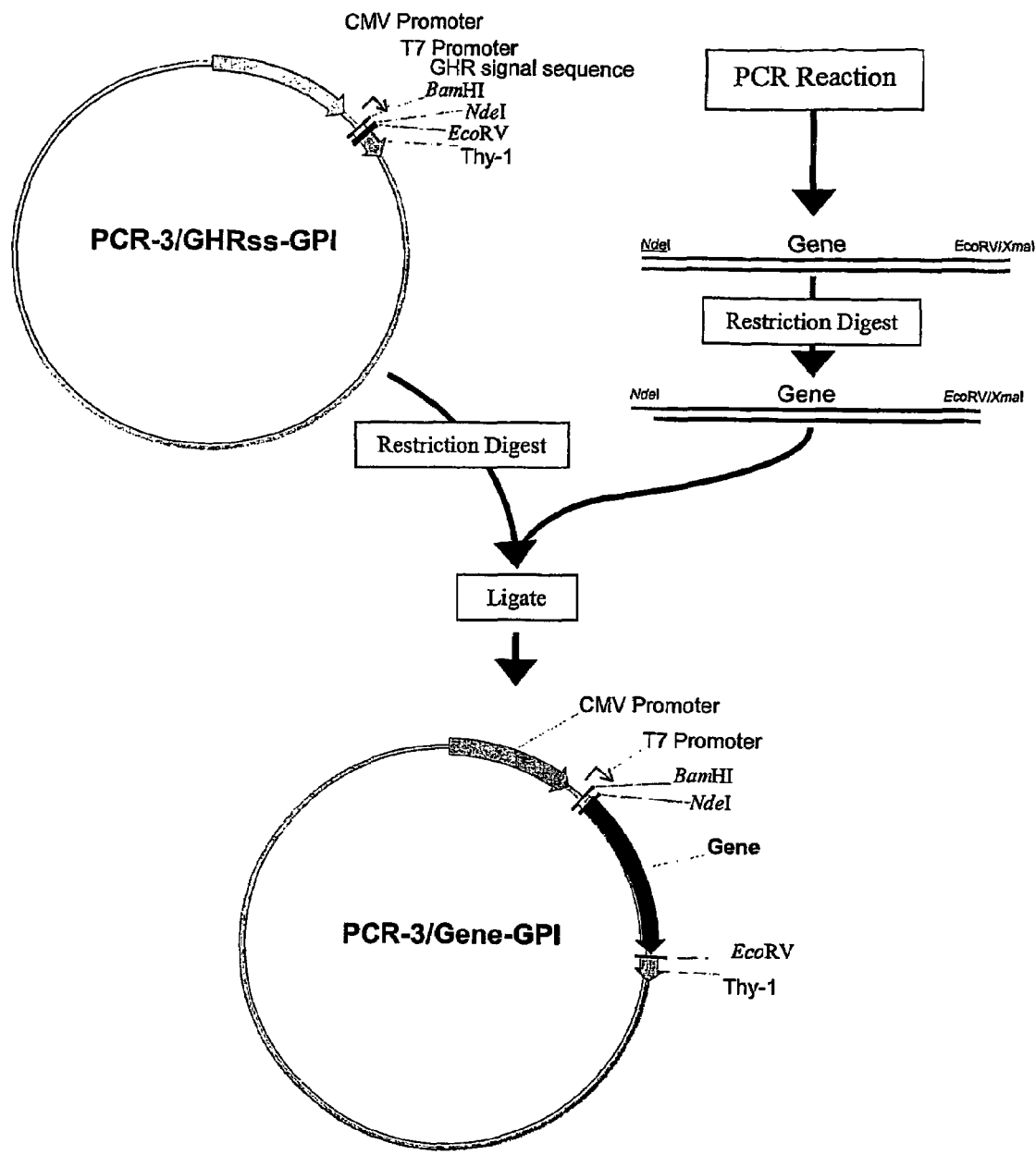

Nucleotide Sequence ggatcctctagactcgaggtcctacaggtATGgatctctggcagctgctgttgacct
tggcactggcaggatcaagtgatgctcatatgTTCCCAACCATTCCCTTATCCAGGC
TTTTTGACAACGCTAGTCTCCGCGCCCATCGTCTGCACCAGCTGGCCTTTGACACCT
ACCAGGAGTTTGAAGAAGCCTATATCCCAAAGGAACAGAAGTATTCATTCCTGCAGA
ACCCCCAGACCTCCCTCTGTTTCTCAGAGTCTATTCCGACACCCTCCAACAGGGAGG
AAACACAACAGAAATCCAACCTAGAGCTGCTCCGCATCTCCCTGCTGCTCATCCAGT
CGTGGCTGGAGCCCGTGCAGTTCCTCAGGAGTGTCTTCGCCAACAGCCTGGTGTACG
GCGCCTCTGACAGCAACGTCTATGACCTCCTAAAGGACCTAGAGGAAGGCATCCAAA
CGCTGATGGGGAGGCTGGAAGATGGCAGCCCCCGGACTGGGCAGATCTTCAAGCAGA
CCTACAGCAAGTTCGACACAAACTCACACAACGATGACGCACTACTCAAGAACTACG
GGCTGCTCTACTGCTTCAGGAAGGACATGGACAAGGTCGAGACATTCCTGCGCATCG
TGCAGTGCCGCTCTGTGGAGGGCAGCTGTGGCTTCggcggtggagggga*t*ATCGACA
*AGCTGGTCAAGTGTGGCGGCATAAGCCTGCTGGTTCAGAACACATCCTGGATGCTGC*
*TGCTGCTGCTTTCCCTCTCCCTCCTCCAAGCCCTAGACTTCATTTCTCTGTGA*

Amino Acid Sequence

MDLWQLLLTLALAGSSDAHMFPTIPLSRLFDNASLRAHRLHQLAFDTYQEFEEAYIP
KEQKYSFLQNPQTSLCFSESIPTPSNREETQQKSNLELLRISLLLIQSWLEPVQFLR
SVFANSLVYGASDSNVYDLLKDLEEGIQTLMGRLEDGSPRTGQIFKQTYSKFDTNSH
NDDALLKNYGLLYCFRKDMDKVETFLRIVQCRSVEGSCGFGGGG*DIDKLVKCGGISL*
*LVQNTSWMLLLLLSLSLLQALDFISL**

Figure 2

Nucleotide Sequence cgatcctctagactcgaggtcctacaggtATGgatctctggcagctgctgttgacct
tggcactggcaggatcaagtgatgctcatatgTTCCCAACCATTCCCTTATCCAGGC
TTTTTGACAACGCTAGTCTCCGCGCCCATCGTCTGCACCAGCTGGCCTTTGACACCT
ACCAGGAGTTTGAAGAAGCCTATATCCCAAAGGAACAGAAGTATTCATTCCTGCAGA
ACCCCCAGACCTCCCTCTGTTTCTCAGAGTCTATTCCGACACCCTCCAACAGGGAGG
AAACACAACAGAAATCCAACCTAGAGCTGCTCCGCATCTCCCTGCTGCTCATCCAGT
CGTGGCTGGAGCCCGTGCAGTTCCTCAGGAGTGTCTTCGCCAACAGCCTGGTGTACG
GCGCCTCTGACAGCAACGTCTATGACCTCCTAAAGGACCTAGAGGAAGGCATCCAAA
CGCTGATGGGGAGGCTGGAAGATGGCAGCCCCGGACTGGGCAGATCTTCAAGCAGA
CCTACAGCAAGTTCGACACAAACTCACACAACGATGACGCACTACTCAAGAACTACG
GGCTGCTCTACTGCTTCAGGAAGGACATGGACAAGGTCGAGACATTCCTGCGCATCG
TGCAGTGCCGCTCTGTGGAGGGCAGCTGTGGCTTCGGCGGCCGCGGTGGCGGAGGTA
GTGGTGGCGGAGGTAGCGGTGGCGGAGGTTCTGGTGGCGGAGGTTCCGAATTCTTTT
CTGGAAGTGAGGCCACAGCAGCTATCCTTAGCAGAGCACCCTGGAGTCTGCAAAGTG
TTAATCCAGGCCTAAAGACAAATTCTTCTAAGGAGCCTAAATTCACCAAGTGCCGTT
CACCTGAGCGAGAGACTTTTTCATGCCACTGGACAGATGAGGTTCATCATGGTACAA
AGAACCTAGGACCCATACAGCTGTTCTATACCAGAAGGAACACTCAAGAATGGACTC
AAGAATGGAAAGAATGCCCTGATTATGTTTCTGCTGGGGAAAACAGCTGTTACTTTA
ATTCATCGTTTACCTCCATCTGGATACCTTATTGTATCAAGCTAACTAGCAATGGTG
GTACAGTGGATGAAAAGTGTTTCTCTGTTGATGAAATAGTGCAACCAGATCCACCCA
TTGCCCTCAACTGGACTTTACTGAACGTCAGTTTAACTGGGATTCATGCAGATATCC
AAGTGAGATGGGAAGCACCACGCAATGCAGATATTCAGAAAGGATGGATGGTTCTGG
AGTATGAACTTCAATACAAAGAAGTAAATGAAACTAAATGGAAAATGATGGACCCTA
TATTGACAACATCAGTTCCAGTGTACTCATTGAAAGTGGATAAGGAATATGAAGTGC
GTGTGAGATCCAAACAACGAAACTCTGGAAATTATGGCGAGTTCAGTGAGGTGCTCT
ATGTAACACTTCCTCAGATGAGCCAATTTACATGTGAAGAAGATTTCTACggcggtg
gaggcccATCGACAAGCTGGTCAAGTGTGGCGGCATAAGCCTGCTGGTTCAGAACA
CATCCTGGATGCTGCTGCTGCTGCTTTCCCTCTCCCTCCTCCAAGCCCTAGACTTCA
TTTCTCTGTGA

Amino Acid Sequence

MDLWQLLLTLALAGSSDAHMFPTIPLSRLFDNASLRAHRLHQLAFDTYQEFEEAYIP
KEQKYSFLQNPQTSLCFSESIPTPSNREETQQKSNLELLRISLLLIQSWLEPVQFLR
SVFANSLVYGASDSNVYDLLKDLEEGIQTLMGRLEDGSPRTGQIFKQTYSKFDTNSH
NDDALLKNYGLLYCFRKDMDKVETFLRIVQCRSVEGSCGFGGRGGGSGGGSGGGG
SGGGSEFFSGSEATAAILSRAPWSLQSVNPGLKTNSSKEPKFTKCRSPERETFSCH
WTDEVHHGTKNLGPIQLFYTRRNTQEWTQEWKECPDYVSAGENSCYFNSSFTSIWIP
YCIKLTSNGGTVDEKCFSVDEIVQPDPPIALNWTLLNVSLTGIHADIQVRWEAPRNA
DIQKGWMVLEYELQYKEVNETKWKMMDPILTTSVPVYSLKVDKEYEVRVRSKQRNSG
NYGEFSEVLYVTLPQMSQFTCEEDFYGGGDIDKLVKCGGISLLVQNTSWMLLLLS
LSLLQALDFISL*

Figure 3

Nucleotide Sequence cgatcctctagactcgaggtcctacaggtATGgatctctggcagctgctgttgacct
tggcactggcaggatcaagtgatgctcatatgTTCCCAACCATTCCCTTATCCAGGC
TTTTTGACAACGCTAGTCTCCGCGCCCATCGTCTGCACCAGCTGGCCTTTGACACCT
ACCAGGAGTTTGAAGAAGCCTATATCCCAAAGGAACAGAAGTATTCATTCCTGCAGA
ACCCCCAGACCTCCCTCTGTTTCTCAGAGTCTATTCCGACACCCTCCAACAGGGAGG
AAACACAACAGAAATCCAACCTAGAGCTGCTCCGCATCTCCCTGCTGCTCATCCAGT
CGTGGCTGGAGCCCGTGCAGTTCCTCAGGAGTGTCTTCGCCAACAGCCTGGTGTACG
GCGCCTCTGACAGCAACGTCTATGACCTCCTAAAGGACCTAGAGGAAGGCATCCAAA
CGCTGATGGGGAGGCTGGAAGATGGCAGCCCCCGGACTGGGCAGATCTTCAAGCAGA
CCTACAGCAAGTTCGACACAAACTCACACAACGATGACGCACTACTCAAGAACTACG
GGCTGCTCTACTGCTTCAGGAAGGACATGGACAAGGTCGAGACATTCCTGCGCATCG
TGCAGTGCCGCTCTGTGGAGGGCAGCTGTGGCTTCGGCGGCCGCGGTGGCGGAGGTA
GTGGTGGCGGAGGTAGCGGTGGCGGAGGTTCTGGTGGCGGAGGTTCCGAATTCTTCC
CAACCATTCCCTTATCCAGGCTTTTTGACAACGCTAGTCTCCGCGCCCATCGTCTGC
ACCAGCTGGCCTTTGACACCTACCAGGAGTTTGAAGAAGCCTATATCCCAAAGGAAC
AGAAGTATTCATTCCTGCAGAACCCCCAGACCTCCCTCTGTTTCTCAGAGTCTATTC
CGACACCCTCCAACAGGGAGGAAACACAACAGAAATCCAACCTAGAGCTGCTCCGCA
TCTCCCTGCTGCTCATCCAGTCGTGGCTGGAGCCCGTGCAGTTCCTCAGGAGTGTCT
TCGCCAACAGCCTGGTGTACGGCGCCTCTGACAGCAACGTCTATGACCTCCTAAAGG
ACCTAGAGGAAGGCATCCAAACGCTGATGGGGAGGCTGGAAGATGGCAGCCCCCGGA
CTGGGCAGATCTTCAAGCAGACCTACAGCAAGTTCGACACAAACTCACACAACGATG
ACGCACTACTCAAGAACTACGGGCTGCTCTACTGCTTCAGGAAGGACATGGACAAGG
TCGAGACATTCCTGCGCATCGTGCAGTGCCGCTCTGTGGAGGGCAGCTGTGGCTTCg
gcggtggaggggatATCGACAAGCTGGTCAAGTGTGGCGGCATAAGCCTGCTGGTTC
AGAACACATCCTGGATGCTGCTGCTGCTGCTTTCCCTCTCCCTCCTCCAAGCCCTAG
ACTTCATTTCTCTGTGA

Amino Acid Sequence

MDLWQLLLTLALAGSSDAHMFPTIPLSRLFDNASLRAHRLHQLAFDTYQEFEEAYIP
KEQKYSFLQNPQTSLCFSESIPTPSNREETQQKSNLELLRISLLLIQSWLEPVQFLR
SVFANSLVYGASDSNVYDLLKDLEEGIQTLMGRLEDGSPRTGQIFKQTYSKFDTNSH
NDDALLKNYGLLYCFRKDMDKVETFLRIVQCRSVEGSCGFGGRGGGGSGGGGSGGGG
SGGGGSEFFPTIPLSRLFDNASLRAHRLHQLAFDTYQEFEEAYIPKEQKYSFLQNPQ
TSLCFSESIPTPSNREETQQKSNLELLRISLLLIQSWLEPVQFLRSVFANSLVYGAS
DSNVYDLLKDLEEGIQTLMGRLEDGSPRTGQIFKQTYSKFDTNSHNDDALLKNYGLL
YCFRKDMDKVETFLRIVQCRSVEGSCGFGGGGDIDKLVKCGGISLLVQNTSWMLLLL
LSLSLLQALDFISL*

Figure 4

| Primer Name | Sequence (5' → 3') |
|---|---|
| GHRss_for1 | gcgcggatcctctagactcgaggtcctac |
| GHRss_rev1 | gcgccatatgagcatcacttgatcctgcg |
| GH2GPI_for1 | gcgccatatgttcccaaccattcccttatc |
| GH2GPI_rev1 | gcgcgatatcccctccaccgccgaagccacagctgccc |
| 1B12GPI_rev1 | gcgccccgggccctccaccgccgtagaaatcttcttcacatg |

Table 1:

Figure 7

CYTOKINE POLYPEPTIDES AND ANTIBODIES CONTAINING A SIGNAL SEQUENCE FOR THE ATTACHMENT OF GLYCOSYLPHOSPHATIDYLINOSITOL

CROSS-REFERENCE TO RELATED APPLICATIONS

This application is a U.S. National Phase of PCT International Application No. PCT/EP2004/001572, filed on Apr. 7, 2004 (published in English under PCT Article 21(2)), which in turn claims the benefit of Great Britain Patent Application No. 0308088.4, filed Apr. 9, 2003, and Great Britain Patent Application No. 0324235.1, filed Oct. 16, 2003.

The invention relates to chimeric recombinant polypeptides, preferably therapeutic polypeptides, which are engineered to include a signal sequence for the attachment of glycosylphosphatidylinositol; cells expressing said polypeptides and methods to manufacture said polypeptides.

GPI-anchors are post-translational modifications to proteins that add glycosyl-phosphatidylinositol which enable these proteins to anchor to the extracellular side of cell membranes. Typically, extracellular proteins which have a GPI anchor do not have transmembrane or cytoplasmic domains. GPI anchor proteins occur in all eukaryotes and form a diverse variety of proteins that includes by example and not by way of limitation, membrane associated enzymes, adhesion molecules and proteins which coat the outer surface of protozoan parasites such as *Trypanosoma brucei* spp. The human kidney includes a number of examples of GPI-anchored proteins i.e. uromodulin, carbonic anhydrase type IV, alkaline phosphatase, Thy-1, BP-3, amino peptidase P, and dipeptidylpeptidase.

All GPI anchor proteins are initially synthesized with a transmembrane anchor which, after trauslocation across the endoplasmic reticulum, is cleaved and covalently linked to a preformed GPI anchor by a specific transamidase enzyme. The modification of proteins by the addition of a GPI-anchor confers important properties on the protein since the addition of the lipid moiety allows the protein to be inserted into cell membranes thereby anchoring the protein thus increasing its effective local concentration.

There are some general requirements for creating a synthetic GPI anchor sequence. These are a hydrophobic region at the C-terminus of the molecule (10-20 amino acids) not followed by a cluster of basic residues, a "spacer domain" of 7-10 residues preceding the hydrophobic region and small amino acids after the spacer region, where cleavage of the precursor and attachment of the anchor occurs. The GPI anchor is preassembled and added to nascent protein in the endoplasmic reticulum.

Concomitant with this step, the initial C-terminal peptide is removed so that the GPI anchor is covalently attached to a new C-terminal amino acid on the protein.

The large scale production of recombinant proteins requires a high standard of quality control since many of these proteins are used as pharmaceuticals, for example: growth hormone; leptin; erythropoietin; prolactin; TNF, interleukins (IL), IL-2, 11-3, IL-4, IL-5, IL-6, IL-7, IL-9, IL-10, IL-11; the p35 subunit of IL-12, IL-13, IL-15; granulocyte colony stimulating factor (G-CSF); granulocyte macrophage colony stimulating factor (GM-CSF); ciliary neurotrophic factor (CNTF); cardiotrophin-1 (CT-1); leukemia inhibitory factor (LIF); oncostatin M (OSM); interferon, IFNa, IFNy, and extracellular receptor domains from any cell surface receptor. Moreover, the development of vaccines, particularly subunit vaccines, (vaccines based on a defined antigen, for example gp120 of HIV), requires the production of large amounts of pure protein free from contaminating antigens which may provoke anaphylaxis.

The production of recombinant protein in cell expression systems is based either on prokaryotic cell expression or eukaryotic cell expression. The latter is preferred when post-translation modifications to the protein are required. Eukaryotic systems include the use of mammalian cells, e.g. Chinese Hamster Ovary cells; insect cells e.g. *Spodoptera* spp; or yeast e.g. *Saccharomyces* spp, *Pichia* spp.

We disclose recombinant proteins which are adapted by the addition of a signal sequence for the attachment of glycosylphosphatidylinositol. Transfected cells expressing said adapted protein retain biological activity and advantageously can be purified with relative ease due to their location in the cell membrane (and/or shedding into the culture media facilitating continuous culture methods) of cells transfected with nucleic acid molecules, typically vectors, which express these proteins.

According to an aspect of the invention there is provided a chimeric polypeptide wherein said polypeptide is engineered to include a domain comprising at least one heterologous signal sequence which sequence directs the attachment of at least one glycosylphosphatidylinositol molecule.

In our co-pending application, PCT/GB02/04665, currently unpublished, we disclose antagonistic chimeric polypeptides which comprise the fusion of a ligand binding domain of a cytokine receptor and a domain which includes a signal sequence for the attachment of glycosylphosphatidylinositol. The content of PCT/GB02/04665 is hereby disclaimed with respect to the present application.

In a further preferred embodiment of the invention said domain comprises the amino acid sequence:
PSPTPTETAT PSPTPKPTST PEETEAPSSA TTLISPLSLI VIFISFVLLI (SEQ ID NO: 12).

In an alternative preferred embodiment of the invention said domain comprises the amino acid sequence:
LVPRGSIEGR GTS1TAYNSE GESAEFFFLL ILLLLLVLV (SEQ ID NO:13).

In a further alternative preferred embodiment of the invention said domain comprises the amino acid sequence:
TSITAYKSE GESAEFFFLL ILLLLLVLV (SEQ ID NO: 14).

In a preferred embodiment of the invention said polypeptide includes at least one glycosylphosphatidylinositol molecule.

In a further preferred embodiment of the invention said polypeptide is a therapeutic polypeptide.

Typically a therapeutic polypeptide is a polypeptide with agonistic or antagonistic activity.

For example, and not by way of limitation, or suppressor polypeptides (e.g. p53 polypeptide, the APC polypeptide, the DPC-4 polypeptide, the BRCA-1 polypeptide, the BRCA-2 polypeptide, the WT-1 polypeptide, the retinoblastoma polypeptide (Lee, et al. (1987) Nature 329:642), the MMAC-1 polypeptide, the adenomatous polyposis coli protein (U.S. Pat. No. 5,783,666), the deleted in colon carcinoma (DCC) polypeptide, the MMSC-2 polypeptide, the NF-1 polypeptide, nasopharyngeal carcinoma tumour suppressor polypeptide (Cheng, et al. 1998. Proc. Nat. Acad. Sci. 95:3042-3047), the MTS1 polypeptide, the CDK4 polypeptide, the NF-1 polypeptide, the NF2 polypeptide, and the VHL polypeptide.

"Antigenic polypeptides" (e.g. tumour rejection antigens the MACE, BAGE, GAGE and DAGE families of tumour rejection antigens, see Schulz et al Proc Natl Acad Sci USA, 1991, 88, pp 991-993). Antigenic polypeptides also includes polypeptide antigens used in the preparation of vaccines which provide protection against infectious agents. For example, viruses such as Human Immunodeficiency Virus (HIV 1 & 2); Human T Cell Leukaemia Virus (HTLV 1 & 2); Ebola virus; Human Papilloma Virus (e.g. HPV-2, HPV-5, HPV-8, HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus, hepatitis B and C viruses. Antigens derived from pathogenic bacteria such as *Staphylococcus aureus; Staphylococcus epidermidis; Enterococcus faecalis; Mycobacterium tuberculsis; Streptococcus* group B; *Streptoccocus pneumoniae; Helicobacter pylori; Neisseria gonorrhea; Streptococcus* group A; *Borrelia burgdorferi; Coccidiodes immitis; Histoplasma sapsulatum; Neisseria meningitides; Shigella flexneri; Escherichia coli; Haemophilus influenzae.* Antigens derived from parasites such as *Trypanosoma* spp, *Plasmodia* spp, *Schiztosoma* spp; and pathogenic fungi such as *Candida* spp.

Therapeutic polypeptides which are "cytotoxic polypeptides" (e.g. pseudomonas exotoxin, ricin toxin, diptheria toxin).

Therapeutic polypeptides which are "cytostatic polypeptides" (e.g, p21, the retinoblastoma polypeptide, the E2F-Rb polypeptide, cyclin dependent kinase inhibitors such as P16, p15, p18 and p19, the growth arrest specific homeobox (GAX) polypeptide as described in Branellec, et al, see WO97/16459 and WO96/30385.

Therapeutic polypeptides which are "pro-drug" activating polypeptides (e.g. cytosine deaminase).

Therapeutic polypeptides which are "apoptosis inducing" polypeptides (e.g. p53, adenovirus E3-11.6K (10.5K), the adenovirus E4orf4 polypeptide, p53 pathway polypeptides, and caspases.

Therapeutic polypeptides which are "pharmaceutical polypeptides" (cytokines e.g. growth hormone; leptin; erythropoietin; prolactin; TNF, interleukins (IL), IL-2, IL-3, IL-4, IL-5, IL-6, IL-7, IL-9, IL-10, IL-11; the p35 subunit of IL-12, IL-13, IL. 15; granulocyte colony stimulating factor (G-CSF); granulocyte macrophage colony stimulating factor (GM-CSF); ciliary neurotrophic factor (CNTF); cardiotrophin-1 (CT-1); leukemia inhibitory factor (LIF); oncostatin M (OSM); interferon, IFNa and IFNy, and antagonists based on extracellular domain receptor for the above cytokines or fusions of the above cytokines with their cognate extracellular domain receptor.

Therapeutic polypeptides which are "anti-angiogenic" polypeptides (e.g. angiostatin, inhibitors of vascular endothelial growth factor (VEGF) such as Tie 2 (as described in PNAS (USA) (1998) 95:8795-8800), endostatin.

Also included within the scope of therapeutic polypeptides are therapeutic antibodies. Preferably said antibodies are monoclonal antibodies or at least the active binding fragments thereof. Therapeutic antibodies may be antibodies which bind and inhibit the activity of biological molecules, e.g. ligands or receptors.

Monoclonal antibodies may be humanised or chimeric antibodies. The chimeric polypeptide therapeutic antibodies may be fusions with extracellular domain receptor polypeptides.

A chimeric antibody is produced by recombinant methods to contain the variable region of an antibody with an invariant or constant region of a human antibody. A humanised antibody is produced by recombinant methods to combine the complementarity determining regions (CDRs) of an antibody with both the constant (C) regions and the framework regions from the variable (V) regions of a human antibody.

In a preferred embodiment of the invention said fragment is a Fab fragment.

In a further preferred embodiment of the invention said antibody is selected from the group consisting of: F(ab')$_2$, Fab, Fv and Fd fragments; and antibodies comprising CDR3 regions.

Preferably said fragments are single chain antibody variable regions (scFV's)• or domain antibodies. If a hybridoma exists for a specific monoclonal antibody it is well within the knowledge of the skilled person to isolate scFv's from mRNA extracted from said hybridoma via RT PCR. Alternatively, phage display screening can be undertaken to identify clones expressing scFv's. Domain antibodies are the smallest binding part of an antibody (approximately 13 kDa). Examples of this technology is disclosed in U.S. Pat. No. 6,248,516, U.S. Pat. No. 6,291,158, U.S. Pat. No. 6,127,197 and EP0368684 which are all incorporated by reference in their entirety.

A modified antibody, or variant antibody, and reference antibody, may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine; d) arginine and lysine; e) isoleucine, leucine, methionine and valine and f) phenylalanine, tyrosine and tryptophan. Most highly preferred are variants which show enhanced biological activity.

In a further preferred embodiment of the invention said therapeutic antibody, or active binding fragment thereof is fused, by a linking molecule, to said domain comprising a heterologous signal sequence which sequence directs the attachment of at least one glycosylphosphatidylinositol molecule. Preferably said linking molecule is a peptide linking molecule.

Peptide linking molecules are known in the art, for example, repeats of the sequence Gly Gly Gly Gly Ser. For example, linking molecules which comprise, 1, 2, 3 or 4 repeats of said sequence. Linking molecules are described in WO01/96565. Linking molecules may be flexible or rigid.

It is known that there are problems associated with the production of binding fragments of antibodies, in particular scFV's. The fragments have a tendency to aggregate in solution making their production on a large scale problematic. The fusion of a domain comprising a glycosylphosphatidylinositol motif to a scFV's would facilitate production and purification.

In a further preferred embodiment of the invention there is provided a polypeptide according to the invention which has been modified by addition, deletion or substitution of at least one amino acid residue to provide a sequence variant of the polypeptide according to the invention.

Typically, variants include chimeras specifically modified to alter a feature of the polypeptide unrelated to its physiological activity. For example, cysteine residues can be substituted or deleted to prevent unwanted disulfide linkages. Similarly, certain amino acids can be changed to enhance expression of the chimera by eliminating proteolysis by proteases in an expression system.

The skilled person will also realize that conservative amino acid substitutions may be made in the chimeric polypeptides to provide functionally equivalent variants of the foregoing polypeptides, (i.e. the variants retain the functional capabilities of the chimeras). As used herein, a "conservative amino acid substitution" refers to an amino acid substitution which does not deleteriously alter the relative charge, hydrophobicity or size characteristics of the protein in which the amino acid substitution is made.

Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. (Q, N can be included, in some instances where size and polarity are conserved, but chelation is unimportant).

Conservative amino-acid substitutions in the amino acid sequence of chimeric polypeptides to produce functionally equivalent variants of these polypeptides typically are made by alteration of a nucleic acid encoding the chimera. Such substitutions can be made by a variety of methods known to one of ordinary skill in the art. For example, amino acid substitutions may be made by PCR-directed mutation, site-directed mutagenesis according to the method of Kunkel, *Proc. Nat. Acad. Sci. U.S.A.* 82: 488-492, 1985.

Alternatively, or preferably, said modification includes the use of modified amino acids in the production of recombinant or synthetic forms of chimeric polypeptides according to the invention. It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, ornithine.

Modifications which alter the biological activity of a polypeptide according to the invention are also within the scope of the invention, for example, a modification which converts an agonist to an antagonist, sometimes referred to as a dominant negative mutation, or produces a super agonist. In our co-pending application, PCT/GB02/005523, currently unpublished, we disclose a variant growth hormone polypeptide that acts as an antagonist. The polypeptide disclosed in PCT/GB02/005523, which is incorporated by reference, is a chimeric polypeptide comprising at least one modified binding domain of growth hormone (GH) and a growth hormone binding domain of a growth hormone receptor (GHR).

Modified GH's are disclosed in U.S. Pat. No. 5,849,535 which is incorporated by reference. The modification to GH is at both site 1 and site 2 binding sites. The modifications to site 1 produce a GH molecule which has a higher affinity for GHR compared to wild-type GH. These modified GH molecules act as agonists. There is also disclosure of site 2 modifications which result in the creation of GH antagonists. Further examples of modifications to GH which alter the binding affinity of GH for site 1 are disclosed in U.S. Pat. No. 5,854,026; U.S. Pat. No. 6,004,931; U.S. Pat. No. 6,022,711; U.S. Pat. No. 6,057,292; and U.S. Pat. No. 6,136,563 each of which are incorporated by reference. Modifications to site 2 are also disclosed, in particular amino acid residue G120 in GH which when modified to either arginine, lysine, tryptophan, tyrosine, phenylalanine, or glutamic acid creates a GH molecule with antagonistic properties. PCT/GB02/005523 discloses chimeric polypeptides which comprise modified growth hormone fused to the extracellular binding domain of growth hormone receptor. The chimera acts as an antagonist and has the property of reduced systemic clearance when administered to a patient in need of GH antagonist therapy.

The current application modifies those GH variants disclosed in U.S. Pat. No. 5,849,535, U.S. Pat. No. 5,854,026; U.S. Pat. No. 6,004,931; U.S. Pat. No. 6,022,711; U.S. Pat. No. 6,057,292; and U.S. Pat. No. 6,136,563 by the inclusion of a domain which comprises a heterologous signal sequence which directs the attachment of glycosylphosphatidylinositol. The current application also modifies the chimeric GH antagonist disclosed in PCT/GB02/005523 by the inclusion of said signal sequence for the attachment of glycosylphosphatidylinositol.

In a yet further preferred embodiment of the invention there is provided a polypeptide wherein said polypeptide comprises at least two polypeptides according to the invention which two polypeptides are linked via a linking molecule. Preferably said linking molecule is a flexible linker. Alternatively said linking molecule is a rigid linker.

Preferably the linker comprises at least one copy of the peptide:

Gly Gly Gly Gly Ser (hereinafter referred to as "Gly4Ser"; SEQ ID NO: 15).

In a further preferred embodiment of the invention said linker comprises at least 2, 3, 4 or 5 copies of said Gly4Ser linker.

In a yet further preferred embodiment of the invention said linker further comprises a protease sensitive site. Preferably said cleavage site is sensitive to a serum protease.

Preferably said cleavage site comprises the amino acid sequence: LVPRGS (SEQ ID NO: 16), or variant thereof.

In a further preferred embodiment of the invention said cleavage site comprises at least one copy of the amino acid sequence: SGGGG (SEQ ID NO: 17), or functional variant thereof. Preferably, said cleavage site comprises the amino acid sequence PGISGGGGGG (SEQ ID NO: 18).

More preferably still said cleavage site comprises the amino acid sequence: LVPRGS PGISGGGGG (SEQ ID NO: 19), or variant thereof.

Alternatively, said cleavage site comprises at least two copies of the amino acid sequence SGGGG (SEQ ID NO: 17), or functional variant thereof, which flank said cleavage site.

In a further preferred embodiment of the invention said cleavage site is sensitive to the serum protease thrombin.

In a yet further preferred embodiment of the invention there is provided an oligomeric polypeptide molecule comprising a plurality of polypeptides according to the invention.

In a preferred embodiment said protein comprises at least 3, 4, 5, 6, 7, 8, 9, or 10 polypeptides according to the invention.

According to a further aspect of the invention there is provided a nucleic acid molecule comprising a nucleic acid sequence which encodes a chimeric polypeptide according to the invention.

According to a yet further aspect of the invention there is provided a vector comprising a nucleic acid molecule according to the invention.

In a preferred embodiment of the invention said vector is an expression vector adapted for eukaryotic gene expression.

Typically said adaptation includes, the provision of transcription control sequences (promoter/enhancer sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and are therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites (e.g. glucose, lipids), environmental effectors (e.g. heat).

Promoter elements also include so called TATA box and RNA polymerise initiation selection (RIS) sequences which function to select a site of transcription initiation. These sequences also bind polypeptides which function, inter alia, to facilitate transcription initiation selection by RNA polymerise.

Adaptations also include the provision of selectable markers and autonomous replication sequences which both facilitate the maintenance of said vector in either the eukaryotic cell. Vectors which are maintained autonomously are referred to as episomal vectors.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sambrook et al. (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al., Current Protocols in Molecular Biology, John Wiley & Sons, Inc. (1994).

It will be apparent to one skilled in the art that the vectors according to the invention could be gene therapy vectors. Gene therapy vectors are typically virus based. A number of viruses are commonly used as vectors for the delivery of exogenous genes. Commonly employed vectors include recombinantly modified enveloped or non-enveloped DNA and RNA viruses, preferably selected from baculoviridiae, parvoviridiae, picornoviridiae, herpesveridiae, poxyiridiae, adenoviridiae, or picomnaviridiae. Chimeric vectors may also be employed which exploit advantageous elements of each of the parent vector properties (See e.g., Feng, et al. (1997) Nature Biotechnology 15:866-870). Such viral vectors may be wild-type or may be modified by recombinant DNA techniques to be replication deficient, conditionally replicating or replication competent.

Preferred vectors are derived from the adenoviral, adeno-associated viral and retroviral genomes. In the most preferred practice of the invention, the vectors are derived from the human adenovirus genome. Particularly preferred vectors are derived from the human adenovirus serotypes 2 or 5. The replicative capacity of such vectors may be attenuated (to the point of being considered "replication deficient") by modifications or deletions in the E1a and/or E1b coding regions. Other modifications to the viral genome to achieve particular expression characteristics or permit repeat administration or lower immune response are preferred.

Alternatively, the viral vectors may be conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342-343; Russell, and S. J. (1994) Eur. J. of Cancer 30A(8): 1165-1171. Additional examples of selectively replicating vectors include those vectors wherein a gene essential for replication of the virus is under control of a promoter which is active only in a particular cell type or cell state such that in the absence of expression of such gene, the virus will not replicate. Examples of such vectors are described in Henderson, et al., U.S. Pat. No. 5,698,443 issued Dec. 16, 1997 and Henderson, et al., U.S. Pat. No. 5,871,726 issued Feb. 16, 1999 the entire teachings of which are herein incorporated by reference.

Additionally, the viral genome may be modified to include inducible promoters which achieve replication or expression only under certain conditions. Examples of inducible promoters are known in the scientific literature (See, e.g. Yoshida and Hamada (1997) Biochem. Biophys. Res. Comm. 230: 426-430; Iida, et al. (1996) J. Virol. 70(9): 6054-6059; Hwang, et al. (1997) J. Virol. 71(9): 7128-7131; Lee, et al. (1997) Mol. Cell. Biol. 17(9): 5097-5105; and Dreher, et al. (1997) J. Biol. Chem. 272(46): 29364-29371.

Vectors may also be non-viral and are available from a number of commercial sources readily available to a person skilled in the art. For example, the vectors may be plasmids which can be episomal or integrating.

According to a further aspect of the invention there is provided a cell transfected with the vector or nucleic acid molecule according to the invention.

In a preferred embodiment of the invention said cell is a eukaryotic cell. Preferably said eukaryotic cell is selected from the group consisting of: a fungal cell e.g. *Saccharomyces cerevisiae, Pichia* spp; slime mold (e.g. *Dictyostelium* spp); insect cell (e.g. *Spodoptera frugiperda*); a plant cell; or a mammalian cell (e.g., CHO cell).

Methods to transfect cells, in particular eukaryotic cells, are well known in the art.

Transfection methods to introduce DNA into cells typically involve the use of chemical reagents, cationic lipids or physical methods. Chemical methods which facilitate the uptake of DNA by cells include the use of DEAE-Dextran (Vaheri and Pagano (1965) Science 175: p434). DEAE-Dextran is a negatively charged cation which associates and introduces the DNA into cells but which can result in loss of cell viability. Calcium phosphate is also a commonly used chemical agent which when co-precipitated with DNA introduces the DNA into cells (Graham et al., Virology (1973) 52: p 456).

The use of cationic lipids (e.g. liposomes (Felgner (1987) Proc. Natl. Acad. Sci USA, 84:p 7413)) has become a common method since it does not have the degree of toxicity shown by the above described chemical methods. The cationic head of the lipid associates with the negatively charged nucleic acid backbone of the DNA to be introduced. The lipid/DNA complex associates with the cell membrane and fuses with the cell to introduce the associated DNA into the cell. Liposome mediated DNA transfer has several advantages over existing methods. For example, cells which are recalcitrant to traditional chemical methods are more easily transfected using liposome mediated transfer.

More recently still, physical methods to introduce DNA have become effective means to reproducibly transfect cells. Direct microinjection is one such method which can deliver DNA directly to the nucleus of a cell (Capecchi (1980) Cell, 22:p 479). This allows the analysis of single cell transfectants.

So called "biolistic" methods physically shoot DNA into cells and/or organelles using a particle gun (Neumann (1982) EMBO J, 1: p 841). Electroporation is arguably the most popular method to transfect DNA. The method involves the use of a high voltage electrical charge to momentarily permeabilise cell membranes making them permeable to macromolecular complexes.

More recently still, a method termed immunoporation has become a recognised technique for the introduction of nucleic acid into cells, (see Bildirici et al., Nature (2000) 405, 298). The technique involves the use of beads coated with an antibody to a specific receptor. The transfection mixture includes nucleic acid, typically vector DNA, antibody coated beads and cells expressing a specific cell surface receptor. The coated beads bind the cell surface receptor and when a shear force is applied to the cells the beads are stripped from the cell surface. During bead removal a transient hole is created through which nucleic acid and/or other biological molecules can enter. Transfection efficiency of between 40-50% is achievable depending on the nucleic acid used.

In a further aspect of the invention there is provided a method to prepare a polypeptide according to the invention comprising:

(i) growing a cell transfected with a vector or nucleic acid according to the invention in conditions conducive to the manufacture of said polypeptide; and (ii) purifying said polypeptide from said cell, or its growth environment.

It will be apparent that polypeptides according to the invention can be purified in a number of ways from cells expressing nucleic acids and/or vectors according to the invention. For example, cells maybe isolated from cell growth media followed by proteolytic cleavage of said polypeptide from the cell membrane. Alternatively, polypeptides can be secreted or cleaved in cell culture to release the polypeptide into the surrounding cell growth media. The polypeptides are then subsequently isolated from cell growth media and purified by conventional techniques (e.g. affinity chromatography, ultra centrifugation). Polypeptides can be further processed to remove the glycosylphosphatidylinositol anchor.

According to a yet further aspect of the invention there is provided a cell wherein said cell presents, at least at its cell surface, a polypeptide according to the invention.

It will be apparent to one skilled in the art that cells could be incubated with chimeric polypeptides as herein disclosed which would insert via the glycosylphosphatidylinositol anchor and become localised in the cell membrane. These cells could then act as delivery vehicles for said polypeptides when administered to patients in need of treatment. For example, polypeptides according to the invention could be incubated will red blood cells taken from a patient, which is subsequently re-administered to the patient.

Also polypeptides according to the invention may insert into a cell membrane after administration (i.e. if injected, into a joint or systemically the GPI containing polypeptide may insert into cell membranes. GPI containing cytokine antagonists may be injected into a coronary artery to block a local cytokine effect. A common problem now is restonosis of coronary arteries after they have been dilated blocking the inflammatory response by local injection of a cytokine antagonist is desirable. The insertion could either by through administering peptide itself or getting local expression by applying a DNA encoding for the peptide-GPI.

In a yet further aspect of the invention there is provided a polypeptide, a nucleic acid molecule, a vector or a cell according to the invention for use as a pharmaceutical.

Preferably said polypeptide, nucleic acid molecule, vector or cell is used in a pharmaceutical composition.

When administered the pharmaceuticals/compositions of the present invention is administered in pharmaceutically acceptable preparations. Such preparations may routinely contain pharmaceutically acceptable concentrations of salt, buffering agents, preservatives, compatible carriers, and optionally other therapeutic agents.

The pharmaceuticals/compositions of the invention can be administered by any conventional route, including injection. The administration and application may, for example, be oral, intravenous, intraperitoneal, intramuscular, intracavity, intraarticular, subcutaneous, topical (eyes), dermal (e.g., a cream lipid soluble insert into skin or mucus membrane) or transdermal.

Pharmaceuticals/compositions of the invention are administered in effective amounts. An "effective amount" is that amount of a pharmaceuticals/compositions that alone, or together with further doses or synergistic drugs, produces the desired response. This may involve only slowing the progression of the disease temporarily, although more preferably, it involves halting the progression of the disease permanently. This can be monitored by routine methods or can be monitored according to diagnostic methods.

The doses of the pharmaceuticals/compositions administered to a subject can be chosen in accordance with different parameters, in particular in accordance with the mode of administration used and the state of the subject (i.e. age, sex). When administered, the pharmaceuticals/compositions of the invention are applied in pharmaceutically-acceptable amounts and in pharmaceutically-acceptable compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceuticals/compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceuticals/compositions may contain suitable buffering agents, including: acetic acid in a salt; citric acid in a salt; boric acid in a salt; and phosphoric acid in a salt.

The pharmaceuticals/compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Advantageously, pharmaceutical preparations comprising polypeptides according to the invention are able to form micelles due to the presence of glycosylphosphatidylinositol anchors. The formation of micelles, either in vitro prior to administration, or in vivo, after administration, enables the formation of large complexes which have reduced clearance rates. This allows the use of lower effective doses of polypeptide to be administered thereby reducing harmful side effects.

An analogous effect is shown if the polypeptides according to the invention are incorporated into liposomes. Liposomes are lipid based vesicles which encapsulate a selected therapeutic agent which is then introduced into a patient. The liposome is manufactured either from pure phospholipid or a mixture of phospholipid and phosphoglyceride. Typically liposomes can be manufactured with diameters of less than 200 nm, this enables them to be intravenously injected and able to pass through the pulmonary capillary bed. Furthermore the biochemical nature of liposomes confers permeability across blood vessel membranes to gain access to selected tissues. Liposomes do have a relatively short half-life. So called STEALTH® liposomes have been developed which comprise liposomes coated in polyethylene glycol (PEG). The PEG treated liposomes have a significantly increased half-life when administered intravenously to a patient. In addition, STEALTH® liposomes show reduced uptake in the reticuloendothelial system and enhanced accumulation selected tissues. In addition, so called immuno-liposomes have been develop which combine lipid based vesicles with an antibody or antibodies, to increase the specificity of the delivery of the agent to a selected cell/tissue.

The use of liposomes as delivery means is described in U.S. Pat. No. 5,580,575 and U.S. Pat. No. 5,542,935.

According to a yet further aspect of the invention there is provided a method of treatment of an animal, preferably a human, comprising administering an effective amount of a nucleic acid and/or vector and/or polypeptide and/or cell according to the invention.

An embodiment of the invention will now be described by example only and with reference to the following figures;

FIG. 1 illustrates the cloning strategy to generate GPI linked proteins. The gene of interest is positioned between a NdeI ("sticky" cutter) and EcoRV/XmaI (blunt cutter) restriction sites by PCR. The PCR product is then digested with NdeI and EcoRV/XmaI, the resulting product is ligated between NdeI and EcoRV sites in pCR-3/GHRss-GPI to obtain a vector from which a GPI linked protein maybe expressed;

FIG. 2 illustrates the nucleotide (SEQ ID NO: 1) and amino acid sequence (SEQ ID NO: 2) of the GH-GPI construct. Sequence from the original pCR-3/GPI vector is shown underlined, linker sequence between the promoter and the initiation codon, ATG, is shown in white on black, (nucleotide sequence SEQ ID NO: 27), and the subsequent GHR signal sequence is in similar colours but italicized (nucleotide sequence (SEQ ID NO: 21, amino acid sequence SEQ ID NO: 22). The GH sequence is shown in CAPITALS (nucleotide sequence SEQ ID NO: 23, amino acid sequence SEQ ID NO: 24) and the link between the GH protein and the GPI anchor shown in black on grey (nucleotide sequence SEQ ID NO: 28, amino acid SEQ ID NO: 29), the GPI anchor signal sequence is shown italicized and underlined (nucleotide sequence SEQ ID NO: 25, amino acid sequence SEQ ID NO: 26). All the relevant restrictions sites are in bold and include BamHI (ggatcc), NdeI (catatg) and EcoRV (gatatc);

FIG. 3 illustrates the nucleotide (SEQ ID NO: 3) and amino acid sequence (SEQ ID NO: 4) of the 1B1-GPI construct (1B1 is GH linked to GHR).

Sequence from the original pCR-3/GPI vector is shown underlined, linker sequence between the promoter and the initiation codon, ATG, is shown in white on black and the subsequent GHR signal sequence is shown in similar colours but italicised. The 1B1 sequence is shown in CAPITALS and the link between the 1B1 protein and the GPI anchor shown in black on grey, the GPI anchor signal sequence is shown italicised and underlined. All the relevant restrictions sites are in bold and include BamHI (ggatcc), NdeI (catatg) and XmaI (cccggg);

FIG. 4 illustrates the nucleotide (SEQ ID NO: 5) and amino acid (SEQ ID NO: 6) sequence of the 1C1-GPI construct (1C1) is GH linked to GH as a tandem).

Figure 5:
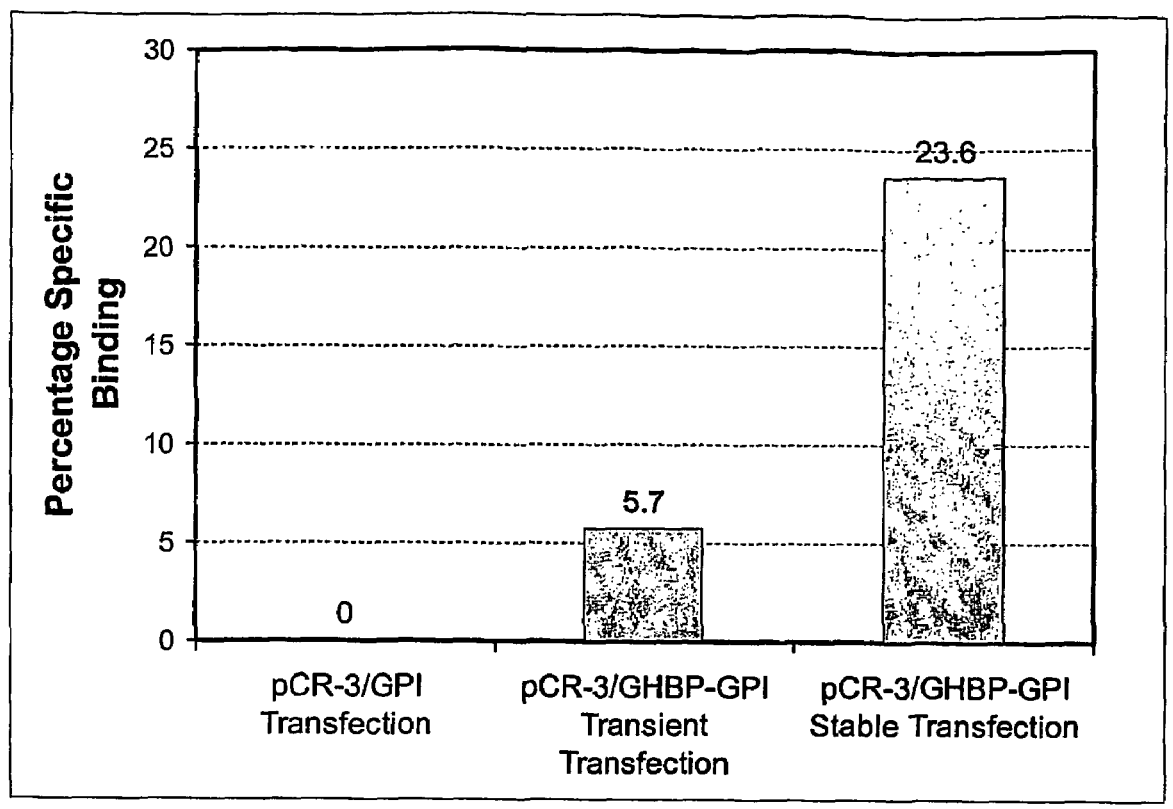
Figure 6:
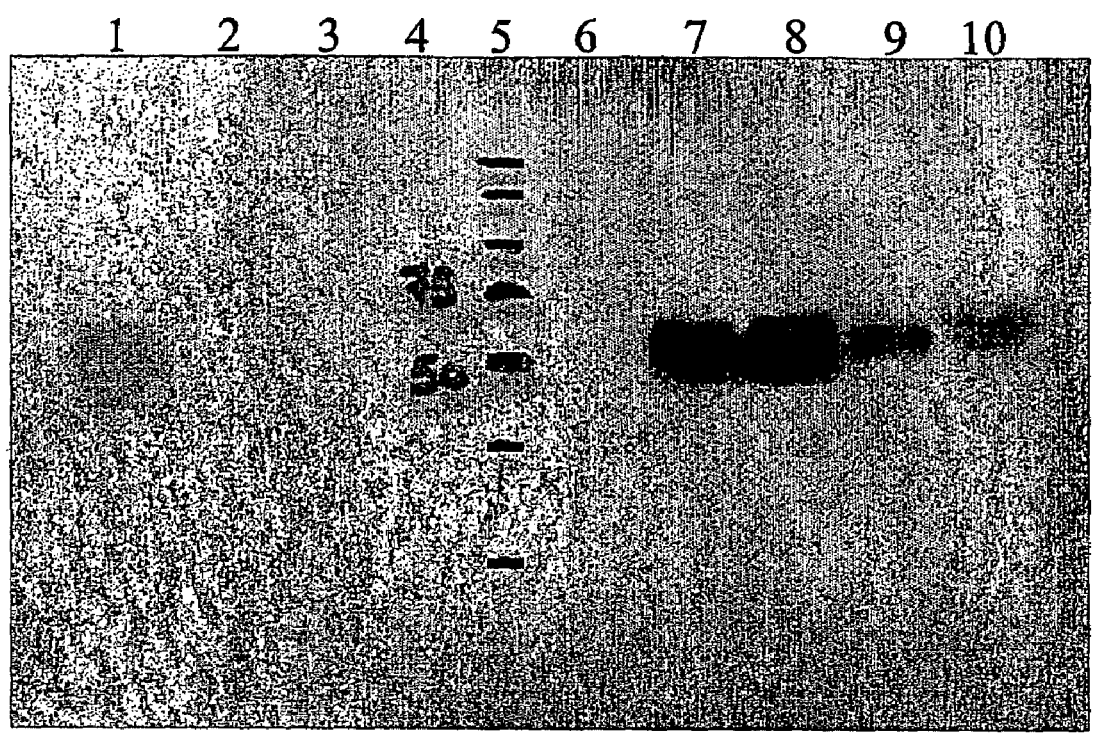

Sequence from the original pCR-3/GPI vector is shown underlined, linker sequence between the promoter and the initiation codon, ATG, is shown in white on black and the subsequent GHR signal sequence is shown in similar colours but italicised. The 1C1 sequence is shown in CAPITALS and the link between the 1C1 protein and the GPI anchor shown in black on grey, the GPI anchor signal sequence is shown italicised and underlined. All the relevant restrictions sites are in bold and include BamHI (ggatcc), NdeI (catatg) and EcoRV (gatatc);

FIG. 5 illustrates a charcoal assay for GHBP. The assay shows a comparison of the amounts of GHBP released into the medium from transient and stable transfected CHO cells after 48 hours. In all cases the medium was concentrated 20 times using a Centricon 30 column prior to the charcoal assay being carried out; and FIG. 6 illustrates a western blot of samples from the membrane purification of GHBP-GPI expressed in CHO cells. The western blot was generating by probing with mouse anti-GHBP antibodies (2C8+263) and then probing with peroxidase labelled anti-mouse IgG. The lanes on the blot contain −1. Positive control: GHBPGPI (stable clone), 2. Untransfected cells (P1), 3. Untransfected cells (P2), 4. Untransfected cells (S1), 5. Molecular weight standards (25, 37, 50, 75, 100, 150, 200 kDa), 6. Medium from untransfected cells, 7. GHBP-GPI (stable clone) (P1), 8. GHBP-GPI (stable clone) (P2), 9. GHBP-GPI (stable clone) (S1) and 10. Medium from GHBP-GPI (stable clone). The blot shows that GHBP-GPI has been purified successfully in the membrane prep (Lane 8).

MATERIALS AND METHODS

Cloning Strategy

The GHR signal sequence was first inserted into the vector, pCR-3/GPI, to enable the subsequently expressed proteins to be targeted to the cell membrane. The GHR signal sequence flanked by a BamHI site and (NdeI EcoRV) sites was obtained by PCR using the primers GHRss_forl and GHRss_revl. This insert was ligated into pCR-3/GPI between the BamHI and EcoRV sites.

The protein of interest was then ligated in-frame between the NdeI and EcoRV restriction sites between the GHR signal sequence and the Thy-1 (GPI anchor signal sequence). PCR was used to generate suitable restriction sites at either end of the gene encoding the protein of interest, a BamHI site was used upstream of the gene and a blunt-cutting restriction enzyme (EcoRV or XmaI) was used downstream of the gene being sub-cloned (FIG. 1).

a) GH-GPI (FIG. 2)

The primers GH2GPI_forl and GH2GPI_revl (Table 1); SEQ ID NOS: 7-11) were used in a PCR reaction to amplify the hGH gene flanked by NdeI and EcoRV sites. The resulting PCR product was digested with these restriction enzymes and then ligated into NdeI/EcoRV double-digested pCR3-GPI. This was then ligated into *E. coli* XL1 Blue cells.

b) 1B1_GPI (FIG. 3). 1B1 is GH linked through its C-terminus to the extracellular domain of the GH receptor and the linked to the GPI signal sequence. Since the 1B 1 gene already contains the EcoRV restriction site, the insert was generated between NdeI and XmaI restriction sites using the primers GH2GPI_forl and 1B12GPI_revl (Table 1). The resulting PCR product was digested with these restriction enzymes and then ligated into NdeI/EcoRV double-digested pCR3-GPI This was then ligated into *E. coli* XL1 Blue cells.

c) 1C1-GPI (FIG. 4). 1C1 is a tandem of GH linked through the second GH C-terminus to the GPI signal sequence. The primers GH2GPI_forl and GH2GPI_revl (Table 1) were used in a PCR reaction to amplify the 1C1 gene flanked by NdeI and EcoRV sites. The resulting PCR product was digested with these restriction enzymes and then ligated into NdeI/EcoRV double-digested pCR3-GPI. This was then ligated into *E. coli* SURE cells.

Transient Transfection into CHO Cells

CHO cells were grown to 70% confluency and then transfected with 3 µg of vector (e.g. pCR-3/GHBP_GPI) using the LT1 Reagent Kit (Corrus Scientific Ltd.). The cells were then grown overnight at 37° C.

Stable Transfection into CHO Cells

CHO cells were grown to 70% confluency and then transfected with 8 µg of vector (e.g. pCR-3/GHBP-GPI) using the Fugene 6 methodology (Roche). After 24 hours incubation the media on the cells was replaced with selective media (CHO cell media with 400 µg/ml G418), if required the cells were split (1:3) onto fresh 100 mm dishes. The dishes were incubated for a further 2-3 days.

The media was once again replaced with selective media, this time with 1000 µg/ml G418 added, and grown for a further 2 days. The cells were then split (1:10) onto fresh dishes with selective media and incubated for a further 4 days. The media was once again replaced with selective media and the dishes incubated for a week. At this point non-transfected cells should have died off leaving only transfected cells. The cells were then processed for FAC sorting/analysis to determine the levels of expression.

Charcoal Assay

This assay is used to determine the amount of binding protein present in a liquid medium.

$I^{125}$ ligand (e.g. $I^{125}$ GH or $I^{125}$ Leptin) was added to a solution containing an unknown amount of binding protein (e.g. GHBP-GPI, Obr-GPI) and was incubated overnight at 4° C. on a rotating wheel. Dextran coated charcoal (Sigma, C-6197) was then added to the tube and this incubated for 15 minutes at room temperature on a rotating wheel. The tube was centrifuged at 13,000 rpm for 12 minutes and the supernatant removed to a new tube. The Total Binding (TB) was then counted using a gamma-counter.

The Non-Specific Binding (NSB) was also measured by repeating the above procedure but adding a large excess of 'cold' ligand in addition to the $I^{125}$ ligand. $I^{125}$ ligand alone was also processed in this way, however the dextran-coated charcoal was not added to this sample, this gave the Total Counts (TC).

The Percentage Specific Binding (PSB) was calculated using the following formula: $PSB=(TB-NSB/TC)\times 100$. For each sample the charcoal assay was done in triplicate and the mean PSB reported with the calculated standard error.

This assay was used to measure the amount of GHBP released in the medium from cells transfected (transient and stable) with pCR 3/GHBP-GPI after 48 hours, the medium was concentrated 20 times using a Centricon 30 column prior to being assayed. Medium from cells transfected with pCR-3/GPI was also processed in the same way (FIG. 5).

Purification a) Preparation of Soluble and Membranes Fractions from CHO-K1 Cell Line Stably Expressing GHBP-GPI CHO-Ki cells either non-transfected or expressing GHBP-GPI were grown to confluency on 100 cm dishes. After serum starvation for 24-48 hrs the culture medium was removed and concentrated and desalted using a Centricon YM-10 filtration column and frozen at −80° C.

For preparation of membranes the cells were first washed with PBS followed by fresh PBS containing a protease inhibitor cocktail (1 µg/ml aprotinin, antipain, pepstatin, leupeptin, 156.5 µg/ml Benzamidine-HCl and 40 µg/ml PMSF, this is referred to as "PBS complete"). The excess PBS was drained off and the cells scraped from the plates and lysed using a dounce homogeniser.

The lysate was firstly subjected to a low speed spin at 2.5 k rpm for 10 minutes, 4° C. The resultant pellet contains nuclear and cellular debris (P1 fraction). The supernatant (S1 fraction) was cloudy and contained cytosolic and membrane bound fractions. The S1 fraction was collected and subjected to a high speed spin at 40 k rpm for 1 hour, 4° C. The supernatant (S2 fraction, containing soluble cytosolic material) was collected and frozen at −80° C. The pellet (P2 fraction, containing insoluble membrane bound material) was washed with PBS complete and centrifuged again as before.

The P2 fraction was resuspended in PBS complete with the addition of 0.1% (v/v) Triton X-100 and frozen in aliquots −80° C. Expression of GHBP was confirmed by Western blotting using anti GHBP antibodies (FIG. 6).

b) Preparation of GH Affinity Column

GH was covalently coupled to CNBr activated sepharose by the following method: Briefly, 0.5 g of CNBr activated sepharose 4 fast flow (Sigma: C-5338, lot no: 91K1548) was resuspended in 10 ml ice cold 1 mM HCl, the swollen matrix was then washed with 100 ml of the same solution. The washed matrix was then immediately added, to a 3 ml solution of 0.1M NaHCO$_3$/0.5M NaCl, pH 8.3 (coupling buffer) containing a total of 3 mg rhGH. The solution was mixed gently for 2 hrs at room temperature and subsequently washed with coupling buffer. Any remaining active groups were blocked by incubation with 0.2M glycine, pH 8.0 for 2 hrs at room temperature. To remove non-specifically bound protein the matrix was alternately washed with coupling buffer followed by 0.1M sodium acetate/0.5M NaCl, pH 4.5. The matrix was stored in PBS; pH7.4, containing 0.02% NaN$_3$ at 4° C.

c) Purification of GHBP from CHO-K1 Media

The GH-coupled column was equilibrated with 10× column volumes of PBS at 4° C. Concentrated and desalted media containing GHBP was allowed to flow through the column under gravity flow. This process was repeated for up to 4 times. The column was washed with PBS and bound protein eluted with 3M KSCN again under gravity flow. The resultant eluate was desalted and concentrated using an Amicon ultrafree-MC centrifugal filtration unit (30,000 molecular weight cut off) and samples analysed by SDS-PAGE and western blotting techniques.

This methodology was also utilised to purify membrane bound protein, however 0.1% Triton was present in all buffers.

The invention claimed is:

1. A polypeptide comprising a domain that directs the attachment of a glycosylphosphatidylinositol molecule, wherein said polypeptide comprises a modified human growth hormone polypeptide comprising a substitution of glycine 120 with arginine in the amino acid sequence set forth in SEQ ID NO: 24 and wherein said domain comprises the amino acid sequence selected from the group consisting of SEQ ID NO: 12, SEQ ID NO: 13 and SEQ ID NO: 14.

2. The polypeptide according to claim 1 wherein said domain comprises the amino acid sequence set forth in SEQ ID NO: 12.

3. The polypeptide according to claim 1 wherein said domain comprises the amino acid sequence set forth in SEQ ID NO: 13.

4. The polypeptide according to claim 1 wherein said domain comprises the amino acid sequence set forth in SEQ ID NO: 14.

5. The polypeptide according to claim 1 wherein said polypeptide comprises at least one glycosylphosphatidylinositol molecule.

* * * * *

UNITED STATES PATENT AND TRADEMARK OFFICE
CERTIFICATE OF CORRECTION

PATENT NO. : 7,625,998 B2 Page 1 of 1
APPLICATION NO. : 10/552388
DATED : December 1, 2009
INVENTOR(S) : Ross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 451 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 20

<210> SEQ ID NO 1
<211> LENGTH: 794
<212> TYPE: DNA
<213> ORGANISM: Artificial sequence
<220> FEATURE:
<223> OTHER INFORMATION: fusion protein comprising growth hormone fused
      to domain comprising glycosylphosphatidyinositol

<400> SEQUENCE: 1
ggatcctcta gactcgaggt cctacaggta tggatctctg gcagctgctg ttgaccttgg      60
cactggcagg atcaagtgat gctcatatgt tcccaaccat tcccttatcc aggcttttg     120 acaacgctag tctccgcgcc catcgtctgc accagctggc ctttgacacc taccaggagt    180
ttgaagaagc ctatatccca aaggaacaga agtattcatt cctgcagaac ccccagacct    240
ccctctgttt ctcagagtct attccgacac cctccaacgg ggaggaaaca caacagaaat    300
ccaacctaga gctgctccgc atctccctgc tgctcatcca gtcgtggctg gagcccgtgc    360
agttcctcag gagtgtcttc gccaacagcc tggtgtacgg cgcctctgac agcaacgtct    420
atgacctcct aaaggaccta gaggaaggca tccaaacgct gatggggagg ctggaagatg    480
gcagcccccg gactgggcag atcttcaagc agacctacag caagttcgac acaaactcac    540
acaacgatga cgcactactc aagaactacg ggctgctcta ctgcttcagg aaggacatgg    600
acaaggtcga gacattcctg cgcatcgtgc agtgccgctc tgtggagggc agctgtggct    660
tcggcggtgg aggggatatc gacaagctgg tcaagtgtgg cggcataagc ctgctggttc    720
agaacacatc ctggatgctg ctgctgctgc tttccctctc cctcctccaa gccctagact    780
tcatttctct gtga                                                     794

<210> SEQ ID NO 2
<211> LENGTH: 254
<212> TYPE: PRT
<213> ORGANISM: Artificial Sequence
<220> FEATURE:
<223> OTHER INFORMATION: fusion protein comprising growth hormone fused
      to a glycosylphosphatidyinositol domain

<400> SEQUENCE: 2

Met Asp Leu Trp Gln Leu Leu Leu Thr Leu Ala Leu Ala Gly Ser Ser
1               5                   10                  15
```

```
Asp Ala His Met Phe Pro Thr Ile Pro Leu Ser Arg Leu Phe Asp Asn
             20                  25                  30

Ala Ser Leu Arg Ala His Arg Leu His Gln Leu Ala Phe Asp Thr Tyr
         35                  40                  45

Gln Glu Phe Glu Glu Ala Tyr Ile Pro Lys Glu Gln Lys Tyr Ser Phe
     50                  55                  60

Leu Gln Asn Pro Gln Thr Ser Leu Cys Phe Ser Glu Ser Ile Pro Thr
 65                  70                  75                  80

Pro Ser Asn Arg Glu Glu Thr Gln Gln Lys Ser Asn Leu Glu Leu Leu
                 85                  90                  95

Arg Ile Ser Leu Leu Leu Ile Gln Ser Trp Leu Glu Pro Val Gln Phe
            100                 105                 110

Leu Arg Ser Val Phe Ala Asn Ser Leu Val Tyr Gly Ala Ser Asp Ser
        115                 120                 125

Asn Val Tyr Asp Leu Leu Lys Asp Leu Glu Glu Gly Ile Gln Thr Leu
    130                 135                 140

Met Gly Arg Leu Glu Asp Gly Ser Pro Arg Thr Gly Gln Ile Phe Lys
145                 150                 155                 160

Gln Thr Tyr Ser Lys Phe Asp Thr Asn Ser His Asn Asp Asp Ala Leu
                165                 170                 175

Leu Lys Asn Tyr Gly Leu Leu Tyr Cys Phe Arg Lys Asp Met Asp Lys
            180                 185                 190

Val Glu Thr Phe Leu Arg Ile Val Gln Cys Arg Ser Val Glu Gly Ser
        195                 200                 205

Cys Gly Phe Gly Gly Gly Asp Ile Asp Lys Leu Val Lys Cys Gly
    210                 215                 220

Gly Ile Ser Leu Leu Val Gln Asn Thr Ser Trp Met Leu Leu Leu Leu
225                 230                 235                 240

Leu Ser Leu Ser Leu Leu Gln Ala Leu Asp Phe Ile Ser Leu
                245                 250
```

<210> SEQ ID NO 3
<211> LENGTH: 1607
<212> TYPE: DNA
<213> ORGANISM: Artificial Sequence
<220> FEATURE:
<223> OTHER INFORMATION: fusion protein comprising growth hormone fused to growth hormone receptor

<400> SEQUENCE: 3

```
ggatcctcta gactcgaggt cctacaggta tggatctctg gcagctgctg ttgaccttgg    60
cactggcagg atcaagtgat gctcatatgt tcccaaccat tcccttatcc aggcttttg   120 acaacgctag tctccgcgcc catcgtctgc accagctggc ctttgacacc taccaggagt   180 tgaagaagc ctatatccca aggaacagaa gtattcatt cctgcagaac cccagacct    240 ccctctgttt ctcagagtct attccgacac cctccaacag gaggaaaaca acagaaaat   300 ccaacctaga gctgctccgc atctccctgc tgctcatcca gtcgtggctg agcccgtgc   360 agttcctcag gagtgtcttc gccaacagcc tggtgtacgg cgcctctgac agcaacgtct   420
atgacctcct aaaggaccta gaggaaggca tccaaacgct gatggggagg ctggaagatg   480 gcagccccg actgggcag atcttcaagc agacctacag caagttcgac acaaactcac   540
acaacgatga cgcactactc aagaactacg gctgctcta ctgcttcagg aaggacatgg   600
acaaggtcga gacattcctg cgcatcgtgc agtgccgctc tgtggagggc agctgtggct   660
tcggcggccg cggtggcgga ggtagtggtg gcggaggtag cggtggcgga ggttctggtg   720
```

-continued

```
gcggaggttc cgaattcttt tctggaagtg aggccacagc agctatcctt agcagagcac    780
cctggagtct gcaaagtgtt aatccaggcc taaagacaaa ttcttctaag gagcctaaat    840
tcaccaagtg ccgttcacct gagcgagaga cttttttcatg ccactggaca gatgaggttc   900
atcatggtac aaagaaccta ggacccatac agctgttcta taccagaagg aacactcaag    960
aatggactca agaatggaaa gaatgccctg attatgtttc tgctggggaa acagctgtt    1020 actttaattc atcgtttacc tccatctgga taccttattg tatcaagcta actagcaatg   1080
gtggtacagt ggatgaaaag tgtttctctg ttgatgaaat agtgcaacca gatccaccca   1140
ttgccctcaa ctggacttta ctgaacgtca gtttaactgg gattcatgca gatatccaag   1200
tgagatggga agcaccacgc aatgcagata ttcagaaagg atggatggtt ctggagtatg   1260
aacttcaata caaagaagta aatgaaacta atggaaaat gatggaccct atattgacaa    1320
catcagttcc agtgtactca ttgaaagtgg ataaggaata tgaagtgcgt gtgagatcca   1380
aacaacgaaa ctctggaaat tatggcgagt tcagtgaggt gctctatgta acacttcctc   1440
agatgagcca atttacatgt gaagaagatt tctacggcgg tggagggga tcgacaagc    1500 tggtcaagtg tggcggcata agcctgctgg ttcagaacac atcctggatg ctgctgctgc   1560
tgctttccct ctccctcctc caagcccctag acttcatttc tctgtga               1607
```

<210> SEQ ID NO 4
<211> LENGTH: 525
<212> TYPE: PRT
<213> ORGANISM: Artificial Sequence
<220> FEATURE:
<223> OTHER INFORMATION: fusion protein comprising growth hormone fused
      to growth hormone receptor

<400> SEQUENCE: 4

```
Met Asp Leu Trp Gln Leu Leu Leu Thr Leu Ala Leu Ala Gly Ser Ser
 1               5                  10                  15

Asp Ala His Met Phe Pro Thr Ile Pro Leu Ser Arg Leu Phe Asp Asn
                20                  25                  30

Ala Ser Leu Arg Ala His Arg Leu His Gln Leu Ala Phe Asp Thr Tyr
            35                  40                  45

Gln Glu Phe Glu Glu Ala Tyr Ile Pro Lys Glu Gln Lys Tyr Ser Phe
        50                  55                  60

Leu Gln Asn Pro Gln Thr Ser Leu Cys Phe Ser Glu Ser Ile Pro Thr
65                  70                  75                  80

Pro Ser Asn Arg Glu Glu Thr Gln Gln Lys Ser Asn Leu Glu Leu Leu
                85                  90                  95

Arg Ile Ser Leu Leu Leu Ile Gln Ser Trp Leu Glu Pro Val Gln Phe
            100                 105                 110

Leu Arg Ser Val Phe Ala Asn Ser Leu Val Tyr Gly Ala Ser Asp Ser
        115                 120                 125

Asn Val Tyr Asp Leu Leu Lys Asp Leu Glu Glu Gly Ile Gln Thr Leu
    130                 135                 140

Met Gly Arg Leu Glu Asp Gly Ser Pro Arg Thr Gly Gln Ile Phe Lys
145                 150                 155                 160

Gln Thr Tyr Ser Lys Phe Asp Thr Asn Ser His Asn Asp Asp Ala Leu
                165                 170                 175

Leu Lys Asn Tyr Gly Leu Leu Tyr Cys Phe Arg Lys Asp Met Asp Lys
            180                 185                 190

Val Glu Thr Phe Leu Arg Ile Val Gln Cys Arg Ser Val Glu Gly Ser
```

Cys Gly Phe Gly Gly Arg Gly Gly Gly Ser Gly Gly Gly Ser
    210                 215                 220
Gly Gly Gly Gly Ser Gly Gly Gly Ser Glu Phe Phe Ser Gly Ser
225                 230                 235                 240
Glu Ala Thr Ala Ala Ile Leu Ser Arg Ala Pro Trp Ser Leu Gln Ser
                245                 250                 255
Val Asn Pro Gly Leu Lys Thr Asn Ser Ser Lys Glu Pro Lys Phe Thr
            260                 265                 270
Lys Cys Arg Ser Pro Glu Arg Glu Thr Phe Ser Cys His Trp Thr Asp
        275                 280                 285
Glu Val His His Gly Thr Lys Asn Leu Gly Pro Ile Gln Leu Phe Tyr
    290                 295                 300
Thr Arg Arg Asn Thr Gln Glu Trp Thr Gln Glu Trp Lys Glu Cys Pro
305                 310                 315                 320
Asp Tyr Val Ser Ala Gly Glu Asn Ser Cys Tyr Phe Asn Ser Ser Phe
                325                 330                 335
Thr Ser Ile Trp Ile Pro Tyr Cys Ile Lys Leu Thr Ser Asn Gly Gly
            340                 345                 350
Thr Val Asp Glu Lys Cys Phe Ser Val Asp Glu Ile Val Gln Pro Asp
        355                 360                 365
Pro Pro Ile Ala Leu Asn Trp Thr Leu Leu Asn Val Ser Leu Thr Gly
    370                 375                 380
Ile His Ala Asp Ile Gln Val Arg Trp Glu Ala Pro Arg Asn Ala Asp
385                 390                 395                 400
Ile Gln Lys Gly Trp Met Val Leu Glu Tyr Glu Leu Gln Tyr Lys Glu
                405                 410                 415
Val Asn Glu Thr Lys Trp Lys Met Met Asp Pro Ile Leu Thr Thr Ser
            420                 425                 430
Val Pro Val Tyr Ser Leu Lys Val Asp Lys Glu Tyr Glu Val Arg Val
        435                 440                 445
Arg Ser Lys Gln Arg Asn Ser Gly Asn Tyr Gly Glu Phe Ser Glu Val
    450                 455                 460
Leu Tyr Val Thr Leu Pro Gln Met Ser Gln Phe Thr Cys Glu Glu Asp
465                 470                 475                 480
Phe Tyr Gly Gly Gly Asp Ile Asp Lys Leu Val Lys Cys Gly Gly
                485                 490                 495
Ile Ser Leu Leu Val Gln Asn Thr Ser Trp Met Leu Leu Leu Leu
            500                 505                 510
Ser Leu Ser Leu Leu Gln Ala Leu Asp Phe Ile Ser Leu
        515                 520                 525

<210> SEQ ID NO 5
<211> LENGTH: 1442
<212> TYPE: DNA
<213> ORGANISM: Artificial Sequence
<220> FEATURE:
<223> OTHER INFORMATION: fusion protein comprising growth hormone fused
      to growth hormone

<400> SEQUENCE: 5
ggatcctcta gactcgaggt cctacaggta tggatctctg gcagctgctg ttgaccttgg      60
cactggcagg atcaagtgat gctcatatgt tcccaaccat tcccttatcc aggcttttg    120 acaacgctag tctccgcgcc catcgtctgc accagctggc ctttgacacc taccaggagt    180

```
ttgaagaagc ctatatccca aaggaacaga agtattcatt cctgcagaac ccccagacct    240
ccctctgttt ctcagagtct attccgacac cctccaacgg gaggaaaaca acagaaaat    300 ccaacctaga gctgctccgc atctccctgc tgctcatcca gtcgtggctg agcccgtgc    360 agttcctcag gagtgtcttc gccaacagcc tggtgtacgg cgcctctgac agcaacgtct    420
atgacctcct aaaggaccta gaggaaggca tccaaacgct gatggggagg ctggaagatg    480 gcagccccg gactgggcag atcttcaagc agacctacag caagttcgac acaaactcac    540
acaacgatga cgcactactc aagaactacg gctgctctac tgcttcagg aaggacatgg    600 acaaggtcga cattcctgc gcatcgtgc agtgccgctc tgtggagggc agctgtggct    660
tcggcggccg cggtggcgga ggtagtggtg gcggaggtag cggtggcgga ggttctggtg    720
gcggaggttc cgaattcttc ccaaccattc ccttatccag gcttttttgac aacgctagtc    780 tccgcgccca tcgtctgcac cagctggcct ttgacaccta ccaggagttt gaagaagcct    840
atatcccaaa ggaacagaag tattcattcc tgcagaaccc ccagacctcc ctctgtttct    900
cagagtctat tccgacaccc tccaacaggg aggaaacaca acagaaatcc aacctagagc    960
tgctccgcat ctccctgctg ctcatccagt cgtggctgga gcccgtgcag ttcctcagga   1020
gtgtcttcgc caacagcctg gtgtacggcg cctctgacag caacgtctat gacctcctaa   1080
aggacctaga ggaaggcatc caaacgctga tggggaggct ggaagatggc agcccccgga   1140
ctgggcagat cttcaagcag acctacagca agttcgacac aaactcacac aacgatgacg   1200
cactactcaa gaactacggg ctgctctact gcttcaggaa ggacatggac aaggtcgaga   1260
cattcctgcg catcgtgcag tgccgctctg tggagggcag ctgtggcttc ggcggtggag   1320
gggatatcga caagctggtc aagtgtggcg gcataagcct gctggttcag aacacatcct   1380
ggatgctgct gctgctgctt ccctctcccc tcctccaagc cctagacttc atttctctgt   1440
ga                                                                 1442
```

<210> SEQ ID NO 6
<211> LENGTH: 470
<212> TYPE: PRT
<213> ORGANISM: Artificial Sequence
<220> FEATURE:
<223> OTHER INFORMATION: fusion protein comprising growth hormone fused
      to growth hormone

<400> SEQUENCE: 6

```
Met Asp Leu Trp Gln Leu Leu Thr Leu Ala Leu Ala Gly Ser Ser
1               5                   10                  15

Asp Ala His Met Phe Pro Thr Ile Pro Leu Ser Arg Leu Phe Asp Asn
                20                  25                  30

Ala Ser Leu Arg Ala His Arg Leu His Gln Leu Ala Phe Asp Thr Tyr
            35                  40                  45

Gln Glu Phe Glu Glu Ala Tyr Ile Pro Lys Gln Lys Tyr Ser Phe
        50                  55                  60

Leu Gln Asn Pro Gln Thr Ser Leu Cys Phe Ser Glu Ser Ile Pro Thr
65                  70                  75                  80

Pro Ser Asn Arg Glu Glu Thr Gln Gln Lys Ser Asn Leu Glu Leu Leu
                85                  90                  95

Arg Ile Ser Leu Leu Leu Ile Gln Ser Trp Leu Glu Pro Val Gln Phe
            100                 105                 110

Leu Arg Ser Val Phe Ala Asn Ser Leu Val Tyr Gly Ala Ser Asp Ser
        115                 120                 125
```

Asn Val Tyr Asp Leu Leu Lys Asp Leu Glu Glu Gly Ile Gln Thr Leu
130                 135                 140

Met Gly Arg Leu Glu Asp Gly Ser Pro Arg Thr Gly Gln Ile Phe Lys
145                 150                 155                 160

Gln Thr Tyr Ser Lys Phe Asp Thr Asn Ser His Asn Asp Asp Ala Leu
                165                 170                 175

Leu Lys Asn Tyr Gly Leu Leu Tyr Cys Phe Arg Lys Asp Met Asp Lys
                180                 185                 190

Val Glu Thr Phe Leu Arg Ile Val Gln Cys Arg Ser Val Glu Gly Ser
                195                 200                 205

Cys Gly Phe Gly Arg Gly Gly Gly Ser Gly Gly Gly Ser
210                 215                 220

Gly Gly Gly Gly Ser Gly Gly Gly Ser Glu Phe Pro Thr Ile
225                 230                 235                 240

Pro Leu Ser Arg Leu Phe Asp Asn Ala Ser Leu Arg Ala His Arg Leu
                245                 250                 255

His Gln Leu Ala Phe Asp Thr Tyr Gln Glu Phe Glu Glu Ala Tyr Ile
                260                 265                 270

Pro Lys Glu Gln Lys Tyr Ser Phe Leu Gln Asn Pro Gln Thr Ser Leu
                275                 280                 285

Cys Phe Ser Glu Ser Ile Pro Thr Pro Ser Asn Arg Glu Glu Thr Gln
290                 295                 300

Gln Lys Ser Asn Leu Glu Leu Leu Arg Ile Ser Leu Leu Leu Ile Gln
305                 310                 315                 320

Ser Trp Leu Glu Pro Val Gln Phe Leu Arg Ser Val Phe Ala Asn Ser
                325                 330                 335

Leu Val Tyr Gly Ala Ser Asp Ser Asn Val Tyr Asp Leu Leu Lys Asp
                340                 345                 350

Leu Glu Glu Gly Ile Gln Thr Leu Met Gly Arg Leu Glu Asp Gly Ser
                355                 360                 365

Pro Arg Thr Gly Gln Ile Phe Lys Gln Thr Tyr Ser Lys Phe Asp Thr
370                 375                 380

Asn Ser His Asn Asp Asp Ala Leu Leu Lys Asn Tyr Gly Leu Leu Tyr
385                 390                 395                 400

Cys Phe Arg Lys Asp Met Asp Lys Val Glu Thr Phe Leu Arg Ile Val
                405                 410                 415

Gln Cys Arg Ser Val Glu Gly Ser Cys Gly Phe Gly Gly Gly Asp
                420                 425                 430

Ile Asp Lys Leu Val Lys Cys Gly Gly Ile Ser Leu Leu Val Gln Asn
                435                 440                 445

Thr Ser Trp Met Leu Leu Leu Leu Ser Leu Ser Leu Leu Gln Ala
                450                 455                 460

Leu Asp Phe Ile Ser Leu
465                 470

<210> SEQ ID NO 7
<211> LENGTH: 29
<212> TYPE: DNA
<213> ORGANISM: Artificial Sequence
<220> FEATURE:
<223> OTHER INFORMATION: growth hormone receptor primer

<400> SEQUENCE: 7
gcgcggatcc tctagactcg aggtcctac                                    29

```
<210> SEQ ID NO 8
<211> LENGTH: 29
<212> TYPE: DNA
<213> ORGANISM: Artificial Sequence
<220> FEATURE:
<223> OTHER INFORMATION: growth hormone receptor primer

<400> SEQUENCE: 8
gcgccatatg agcatcactt gatcctgcg                                              29

<210> SEQ ID NO 9
<211> LENGTH: 30
<212> TYPE: DNA
<213> ORGANISM: Artificial Sequence
<220> FEATURE:
<223> OTHER INFORMATION: primer amplification of human growth hormone

<400> SEQUENCE: 9
gcgccatatg ttcccaacca ttcccttatc                                             30

<210> SEQ ID NO 10
<211> LENGTH: 38
<212> TYPE: DNA
<213> ORGANISM: Artificial Sequence
<220> FEATURE:
<223> OTHER INFORMATION: primer amplification of human growth hormone

<400> SEQUENCE: 10
gcgcgatatc ccctccaccg ccgaagccac agctgccc                                    38

<210> SEQ ID NO 11
<211> LENGTH: 42
<212> TYPE: DNA
<213> ORGANISM: Artificial Sequence
<220> FEATURE:
<223> OTHER INFORMATION: primer for linking growth hormone and growth
      hormone receptor to glycosylphospatidyinositol domain

<400> SEQUENCE: 11
gcgccccggg ccctccaccg ccgtagaaat cttcttcaca tg                               42

<210> SEQ ID NO 12
<211> LENGTH: 50
<212> TYPE: PRT
<213> ORGANISM: Homo sapiens

<400> SEQUENCE: 12

Pro Ser Pro Thr Pro Thr Glu Thr Ala Thr Pro Ser Pro Thr Pro Lys
1               5                   10                  15

Pro Thr Ser Thr Pro Glu Glu Thr Glu Ala Pro Ser Ser Ala Thr Thr
            20                  25                  30

Leu Ile Ser Pro Leu Ser Leu Ile Val Ile Phe Ile Ser Phe Val Leu
        35                  40                  45

Leu Ile
    50

<210> SEQ ID NO 13
<211> LENGTH: 39
<212> TYPE: PRT
<213> ORGANISM: Homo sapiens

<400> SEQUENCE: 13

Leu Val Pro Arg Gly Ser Ile Glu Gly Arg Gly Thr Ser Ile Thr Ala
1               5                   10                  15
```

-continued

Tyr Asn Ser Glu Gly Glu Ser Ala Glu Phe Phe Phe Leu Leu Ile Leu
            20                  25                  30

Leu Leu Leu Leu Val Leu Val
            35

<210> SEQ ID NO 14
<211> LENGTH: 27
<212> TYPE: PRT
<213> ORGANISM: Homo sapiens

<400> SEQUENCE: 14

Thr Ser Ile Thr Ala Tyr Lys Ser Glu Gly Glu Ser Ala Glu Phe Phe
1               5                   10                  15

Phe Leu Leu Ile Leu Leu Leu Leu Val Leu
            20                  25

<210> SEQ ID NO 15
<211> LENGTH: 5
<212> TYPE: DNA
<213> ORGANISM: Artificial Sequence
<220> FEATURE:
<223> OTHER INFORMATION: linker peptide for linking growth hormone with
      growth hormone receptor

<400> SEQUENCE: 15 ggggs                                                                   5

<210> SEQ ID NO 16
<211> LENGTH: 6
<212> TYPE: PRT
<213> ORGANISM: Homo sapiens

<400> SEQUENCE: 16

Leu Val Pro Arg Gly Ser
1               5

<210> SEQ ID NO 17
<211> LENGTH: 5
<212> TYPE: PRT
<213> ORGANISM: Homo sapiens

<400> SEQUENCE: 17

Ser Gly Gly Gly Gly
1               5

<210> SEQ ID NO 18
<211> LENGTH: 10
<212> TYPE: PRT
<213> ORGANISM: Homo sapiens

<400> SEQUENCE: 18

Pro Gly Ile Ser Gly Gly Gly Gly Gly Gly
1               5                   10

<210> SEQ ID NO 19
<211> LENGTH: 16
<212> TYPE: PRT
<213> ORGANISM: Homo sapiens

<400> SEQUENCE: 19

Leu Val Pro Arg Gly Ser Pro Gly Ile Ser Gly Gly Gly Gly Gly Gly
1               5                   10                  15

<210> SEQ ID NO 20

```
-continued
<211> LENGTH: 15
<212> TYPE: PRT
<213> ORGANISM: Artificial Sequence
<220> FEATURE:
<223> OTHER INFORMATION: cleavage sequence

<400> SEQUENCE: 20

Pro Gly Ile Ser Gly Gly Gly Gly Gly Ser Gly Gly Gly Gly
1               5                   10                  15
```